US012636453B1

(12) United States Patent
Hindi

(10) Patent No.: US 12,636,453 B1
(45) Date of Patent: May 26, 2026

(54) ENDOTRACHEAL TUBE EXCHANGER

(71) Applicant: Zakaria Hindi, Springfield, IL (US)

(72) Inventor: Zakaria Hindi, Springfield, IL (US)

( * ) Notice: Subject to any disclaimer, the term of this patent is extended or adjusted under 35 U.S.C. 154(b) by 0 days.

(21) Appl. No.: 19/438,300

(22) Filed: Dec. 31, 2025

(51) Int. Cl.
　　*A61M 16/04* 　　　(2006.01)
　　*A61M 39/10* 　　　(2006.01)

(52) U.S. Cl.
　　CPC .... *A61M 16/0488* (2013.01); *A61M 16/0427* (2014.02); *A61M 16/0463* (2013.01); *A61M 39/10* (2013.01); *A61M 2039/1077* (2013.01); *A61M 2209/06* (2013.01)

(58) Field of Classification Search
　　CPC .......... A61M 16/0488; A61M 16/0427; A61M 2025/0183; A61M 16/0404; A61M 16/0429; A61M 16/0475; A61M 16/0816; A61B 1/00154
　　See application file for complete search history.

(56) References Cited

U.S. PATENT DOCUMENTS

| | | | |
|---|---|---|---|
| 4,416,273 A | 11/1983 | Grimes | |
| 5,507,284 A | 4/1996 | Daneshvar | |

| | | | |
|---|---|---|---|
| 5,694,922 A | 12/1997 | Palmer | |
| 6,443,156 B1 | 9/2002 | Niklason et al. | |
| 7,581,541 B2 | 9/2009 | Madsen et al. | |
| 7,938,118 B2 | 5/2011 | Kessler | |
| 8,991,396 B2 | 3/2015 | Deshpande | |
| 2005/0103332 A1* | 5/2005 | Gingles | A61M 16/0463 604/529 |
| 2008/0066746 A1* | 3/2008 | Nelson | A61M 16/04 128/200.26 |
| 2020/0030558 A1* | 1/2020 | Avniel | A61M 16/0418 |

* cited by examiner

*Primary Examiner* — Margaret M Luarca

(57) ABSTRACT

Disclosed is an Endotracheal Tube Exchanger (ETE) assembly, kit, and/or method which may include an inner tube defining a plurality of openings for receiving a ventilator connector. The inner tube may define an internal airflow passage that may include a proximal opening and a lateral side opening at an intermediate region. A removable cover may overlie the side opening. A side adapter may attach to the lateral opening once the cover may be removed and may include an insertion portion received into the internal passage. The ETT exchange method may include inserting the inner tube through the ETT, connecting the ventilator connector to the top connector, sliding the old ETT proximally, removing the cover, attaching the side adapter, transferring the connection to the side adapter for removing the old ETT, and/or loading a new ETT through the proximal end.

20 Claims, 16 Drawing Sheets

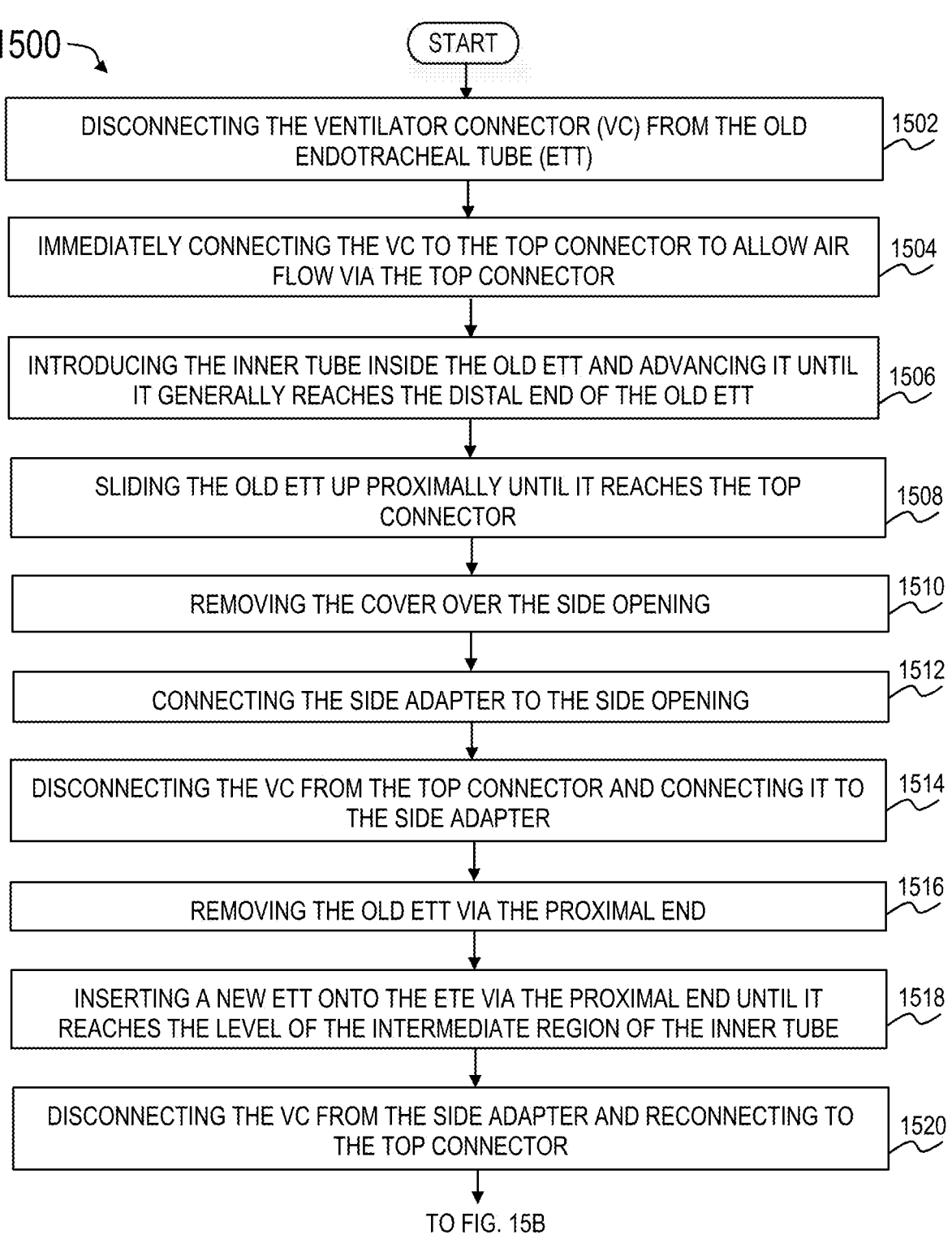

1500

START

DISCONNECTING THE VENTILATOR CONNECTOR (VC) FROM THE OLD ENDOTRACHEAL TUBE (ETT)     1502

IMMEDIATELY CONNECTING THE VC TO THE TOP CONNECTOR TO ALLOW AIR FLOW VIA THE TOP CONNECTOR     1504

INTRODUCING THE INNER TUBE INSIDE THE OLD ETT AND ADVANCING IT UNTIL IT GENERALLY REACHES THE DISTAL END OF THE OLD ETT     1506

SLIDING THE OLD ETT UP PROXIMALLY UNTIL IT REACHES THE TOP CONNECTOR     1508

REMOVING THE COVER OVER THE SIDE OPENING     1510

CONNECTING THE SIDE ADAPTER TO THE SIDE OPENING     1512

DISCONNECTING THE VC FROM THE TOP CONNECTOR AND CONNECTING IT TO THE SIDE ADAPTER     1514

REMOVING THE OLD ETT VIA THE PROXIMAL END     1516

INSERTING A NEW ETT ONTO THE ETE VIA THE PROXIMAL END UNTIL IT REACHES THE LEVEL OF THE INTERMEDIATE REGION OF THE INNER TUBE     1518

DISCONNECTING THE VC FROM THE SIDE ADAPTER AND RECONNECTING TO THE TOP CONNECTOR     1520

FROM FIG. 15A

REMOVING THE SIDE ADAPTER FROM THE LATERAL SIDE OPENING TO CLEAR THE PATH FOR THE NEW ETT   1521

ADVANCING THE NEW ETT UNTIL IT REACHES THE DISTAL END OF THE INNER TUBE   1522

REMOVING THE INNER TUBE WHILE THE VC IS CONNECTED TO THE TOP CONNECTOR   1524

CONNECTING THE VC TO THE CONNECTOR OF THE NEW ETT   1526

END

ENDOTRACHEAL TUBE EXCHANGER

TECHNICAL FIELD

The present disclosure relates generally to medical apparatuses. More specifically, the present disclosure pertains to devices and/or methods associated with exchanging endotracheal tubes.

BACKGROUND

In Intensive Care Units (ICU), some patients may be on endotracheal tubes (ETTs) to receive life-sustaining mechanical ventilation. Given the need for sterility, these ETTs may be disposable and/or single-use. Depending on how long the patient needs to be on ventilation and/or their risk of infection and/or complication, some patients may require exchanging their ETT for several reasons. The tube may have a defect such as cuff leaks, damage to the tube wall, connector problems, and/or defects in the pilot balloon and/or inflation line that may lead to persistent air leak and/or inability to maintain cuff seal. Obstruction of the tube by secretions, blood, and/or kinking may also prompt exchange. In certain situations, ETTs may be exchanged after a period of days on ventilation in an effort to reduce infection risk, including ventilator-associated pneumonia. Failure to exchange a malfunctioning and/or leaking tube can contribute to inadequate ventilation, loss of positive pressure, aspiration around the cuff, and/or ongoing risk of pulmonary complications.

Existing devices and/or processes may suffer from certain limitations. In situations requiring the replacement of an existing ETT with a new one, medical practitioners may follow a conventional practice of exchanging an endotracheal tube. In a typical process, an endotracheal tube exchanger and/or airway exchange catheter may be introduced through the lumen of an existing endotracheal tube. To perform the exchange, medical practitioners may temporarily disconnect the ventilator circuit from the ETT, insert and position the exchanger to a depth approximating the distal tip of the tube, then withdraw the old tube over the exchanger. A new tube may then be advanced over the exchanger into the trachea, after which the exchanger may be removed and/or the ventilator may be reconnected.

However, known devices and/or methods may be limited by the need to interrupt airflow while the exchanger is being inserted and/or repositioned, which can lead to intervals without adequate ventilation. These systems may fail to maintain gas delivery during critical periods of the exchange procedure, which may create conditions that can challenge the stability of a patient with reduced respiratory capacity. A drawback of conventional techniques may be that the transition steps between removing the old tube and/or placing the new tube can be time-critical, particularly when the patient may depend heavily on continuous ventilatory support. Even losing a few seconds without continuous oxygenation may lead to significant medical complications for some patients, such as hypoxemia and/or cardiac arrest.

These existing procedures may also be complicated by failure to advance the new tube, esophageal intubation, loss of the airway, and/or inability to reintubate over the exchanger. In such events, the exchange attempt may be aborted and/or urgent efforts may be directed toward reestablishing a secure airway and/or restoring ventilation by reinserting the old endotracheal tube and/or using alternative airway techniques.

In light of the above, improvements to these and other drawbacks of existing systems are therefore desirable.

BRIEF DESCRIPTION OF THE DRAWINGS

The accompanying drawings, which are incorporated in and constitute a part of this specification, illustrate several embodiments directed to one of ordinary skill in the art and, together with the description, serve to explain the disclosed principles. It should be noted that, in accordance with standard practice in the industry, various features are not drawn to scale. In fact, the dimensions of the various features may be increased or reduced for clarity of discussion. In the drawings:

FIGS. 15A and 15B are a flowchart exemplifying an endotracheal tube exchange process, according to at least one embodiment of the present disclosure.

Figure 1:
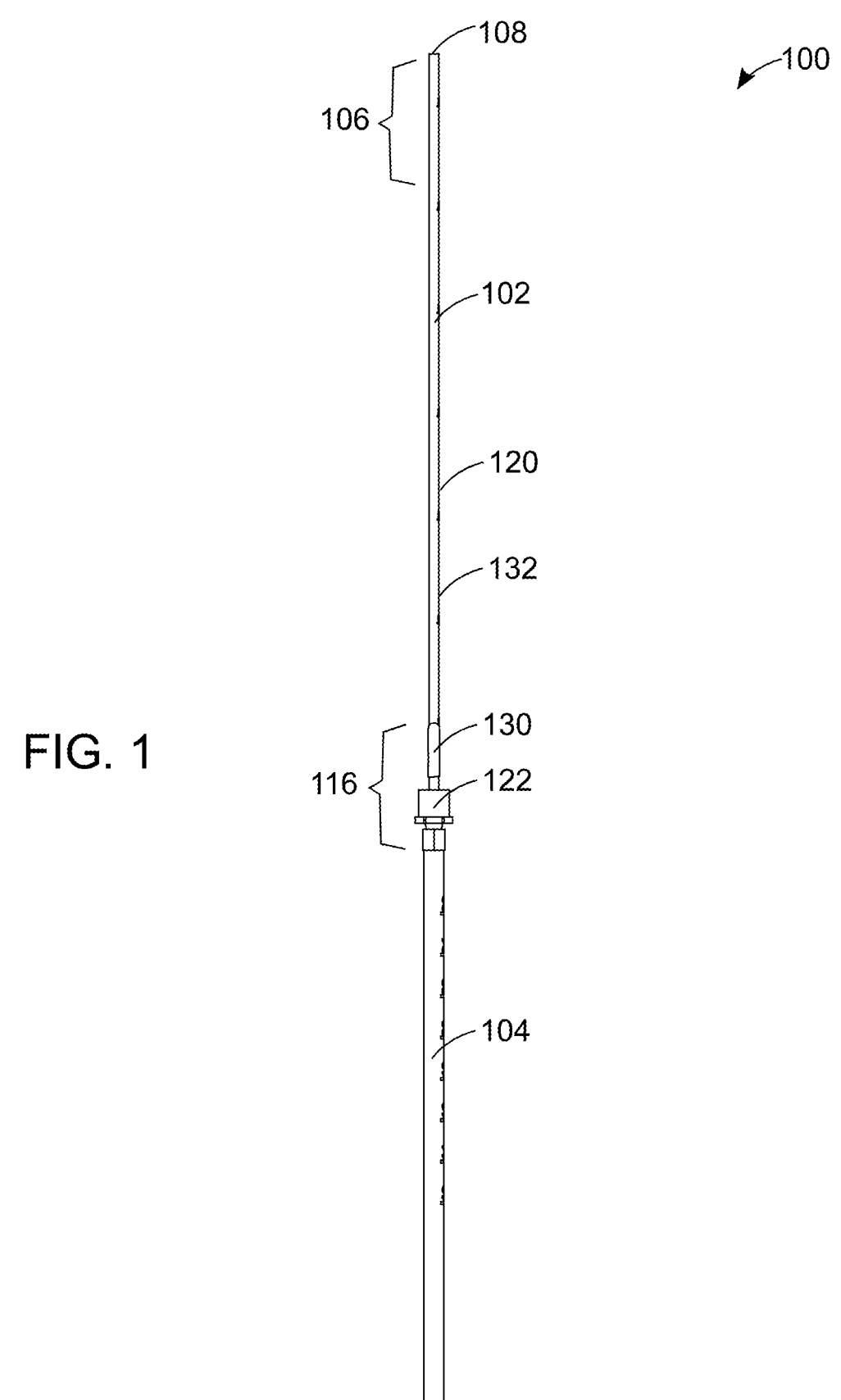
FIG. 1 is a front view of the inner tube of the endotracheal tube exchanger (ETE) assembly inserted into the outer endotracheal tube (ETT), showing the lateral side opening covered by a removable cover, according to at least one embodiment of the present disclosure.

Reference numerals: 100—Endotracheal tube exchanger assembly; 102—Inner tube; 104—Outer endotracheal tube (ETT); 106—Proximal portion; 108—Proximal opening; 110—Distal portion; 112—Distal opening; 114—Internal flow passage; 116—Intermediate region; 118—Lateral side opening; 120—Wall (of inner tube); 122—Top connector; 130—Removable cover; 132—Outer surface (of inner tube); 134—Continuous outer wall surface; 136—Side adapter; 138—Outer connector portion; 140—Ventilator connector; 142—Elongate insertion portion; 143—Surrounding wall (of insertion portion); 144—Internal channel; 145—Inner end (of insertion portion); 146—Distal outlet opening (at insertion tip); 147—Aperture (bottom flow opening).

Like reference numerals refer to like parts throughout the several views of the drawings. Reference numbers that are repeated across plural figures are intended to identify the same features in various implementations. Other features of the present embodiments will be apparent from the accompanying drawings and from the detailed description that follows.

DETAILED DESCRIPTION

All illustrations of the drawings are for the purpose of describing selected versions of the present invention and are not intended to limit the scope of the present invention.

While many aspects and features relate to, and are described in the context of devices that may facilitate Endotracheal Tube (ETT) exchange process, embodiments are not limited to use only in this context. The principles described herein may likely be applied to other environments that may use ventilation and/or controlled atmospheric support. Accordingly, the scope encompasses any device, assembly, system, and/or method configured to use at least one of the structural and/or functional features described herein, regardless of the specific application environment and/or intended use.

Accordingly, the present disclosure is directed to an adaptable Endotracheal Tube Exchanger (ETE) assembly 100 that substantially obviates one or more problems due to limitations and disadvantages of the related art. An objective of the present disclosure is to provide a safer exchange of the ETT via a device, assembly, and/or process in which the patient may receive oxygen from the ventilator while reducing the duration of airflow interruption. In other words, the present disclosure seeks to provide users with a device and/or method that can maintain ventilation and/or oxygenation minimizing any interruption while exchanging an ETT.

The present disclosure achieves this by using an inner tube 102 dimensioned to be slidably received within the ETT lumen. The inner tube 102 may define a proximal opening 108 and an intermediate region 116 with a lateral side opening 118 configured to slidably receive a side adapter 136. This configuration, in which the proximal opening 108 may be dimensioned to receive a ventilator connector (VC), may allow the VC to be interchangeably coupled to the proximal opening 108 and/or the lateral side opening 118 during different phases of the change procedure. Unlike conventional ETT exchangers that may require the provider to disconnect the patient from the ventilator to slide the new ETT and the patient may undergo a longer period of time when airflow must be interrupted, the disclosed configuration may allow the patient to receive airflow with minimal and/or reduced interruption by maintaining continuous connection to the proximal opening 108 and/or lateral side opening 118 throughout the entire ETT exchange process 1500. Moreover, the disclosed embodiments may provide a cost-effective device and/or method and/or an easy-to-use assembly for facilitating the ETT exchange process. Purposes of the present disclosure are not limited to the above-mentioned purpose. Other purposes and advantages of the present disclosure that are not mentioned can be understood based on the following descriptions, and can be more clearly understood based on the following descriptions, and can be more clearly understood based on embodiments of the present disclosure.

In order to accomplish this, the present disclosure comprises an inner tube 102 defining a proximal opening 108, an intermediate side opening 118, and a distal opening 112, a top connector 122, a side adapter 136 configured to be slidably received within the inner tube 102, and/or a removable cover 130 such as tape, according to one embodiment. Broadly, the present disclosure may concern an inner tube 102 dimensioned along a longitudinal axis with an overall length exceeding that of the outer endotracheal tube (ETT) 104. The outer diameter of the inner tube 102 may be less than the inner diameter of the ETT 104, which may result in an annular clearance between the inner tube outer surface and the ETT inner surface when the inner tube 102 may be received within the ETT 104 lumen. The inner tube 102 may define a continuous internal flow passage 114 extending from the proximal opening 108 to the distal opening 112.

In accordance with at least one aspect of the present disclosure, the proximal portion 106 of the inner tube 102 may include a top connector 122 secured thereto surrounding the proximal opening 108. The proximal opening 108 of the inner tube 102 may incorporate a generally tubular body with a top connector 122 corresponding to a standard ETT 104 top adapter 122, dimensioned to mate with a ventilator connector (VC). The internal bore of this top connector 122 may align with and/or form a continuation of the internal passage of the inner tube 102. According to an exemplary embodiment, the inner tube 102 may further define a lateral side opening 118 at an intermediate region 116, spaced from the proximal end and the distal end of the inner tube 102. A side adapter 136 may be attachable to the inner tube 102 at this intermediate region 116. The side adapter 136 may include an outer connector portion 138, which may present a shape similar to the proximal top connector 122, and/or an elongate insertion portion 142. The elongate insertion portion 142 may be sized for receipt through the lateral side opening 118 and/or into the internal passage of the inner tube 102, which may define an internal channel that may terminate in a distal outlet opening 146 bounded by the surrounding wall 143 of the insertion portion 142.

In at least one embodiment, a cover 130 such as an elongate tape element may be positioned around this intermediate region 116 over the lateral side opening 118, which may conform to the inner tube 102 outer surface and/or overlying the lateral side opening 118 to form a continuous outer wall surface 134 segment that may permit slidable movement of the outer endotracheal tube 104 over the cover 130. The relative positioning of the cover 130 is such that, when the distal opening 112 of the inner tube 102 may approach the distal end of the ETT 104, the proximal opening and the lateral side opening 118 may be located outside the patient's airway.

An advantage of this may be providing a safer exchange of an ETT. A benefit achieved through this disclosure may be the process wherein the patient may continue to receive oxygen from the ventilator throughout the tube exchange minimizing airflow interruption and/or while mitigating the risk associated with interrupted airflow. Thus, this disclosure may mitigate the risk of complicating a patient's oxygenation by utilizing the side adapter 136 and the top connector 122 removably coupled to the inner tube. This arrangement may allow the ventilator connector (VC) to be immediately connected to the top connector 122 after disconnection from the old ETT 104 so that air may flow with minimal inter-
ruption through the ETT 122 while the exchange procedure
is being performed. Effects of the present disclosure are not
limited to the above-mentioned effects, and other effects as
not mentioned will be clearly understood by those skilled in
the art from the following descriptions.

Reference will now be made in detail to the disclosed
embodiments, examples of which are illustrated in the
accompanying drawings. In reference to FIG. 1 through
FIG. 14, the present disclosure is an endotracheal tube
exchanger (ETE) assembly 100, comprising an outer endo-
tracheal tube (ETT) 104 extending along a longitudinal axis
from a proximal end to a distal end, wherein the ETT 104
may define a primary lumen dimensioned for tracheal intu-
bation. The ETT 104 may further comprise standard fea-
tures, including a distal cuff secured around an outer surface
of the ETT adjacent the distal end. A pilot balloon assembly
may be connected to the cuff via an inflation lumen. The
ETT side wall in the distal region may define a Murphy eye
opening, bounded circumferentially by the wall of the tube.
A proximal top connector 122 may be fixed at the proximal
end of the ETT, said top connector 122 having a generally
cylindrical body with an external geometry compatible with
standard ventilator connectors and/or an internal bore
aligned with the ETT lumen. As can be seen in FIG. 1, the
inner tube 102 may be disposed within the outer ETT 104
during the exchange process.

Figure 13:
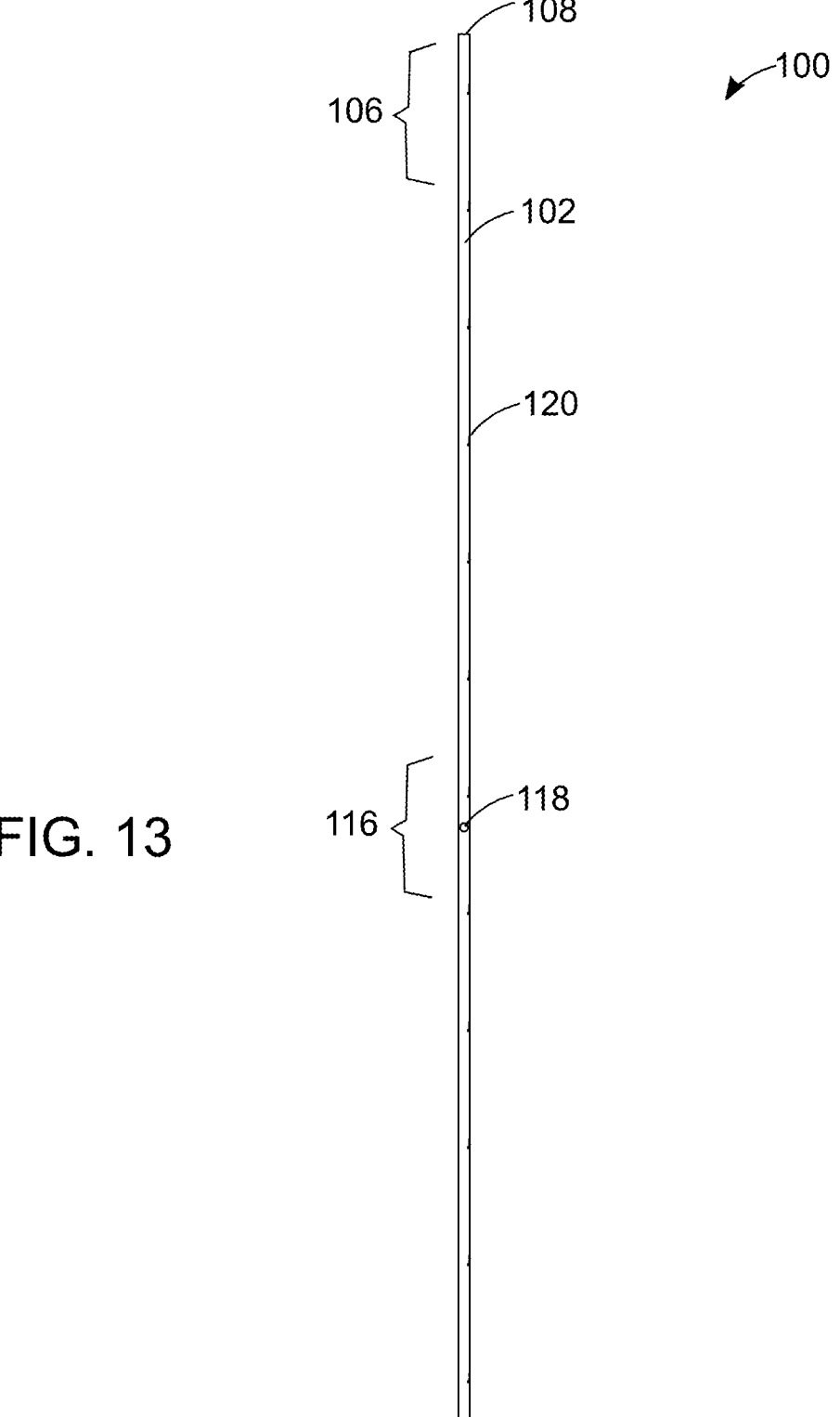
FIG. 13 is a front view of the inner tube, according to at least one embodiment of the present disclosure.
Figure 14:
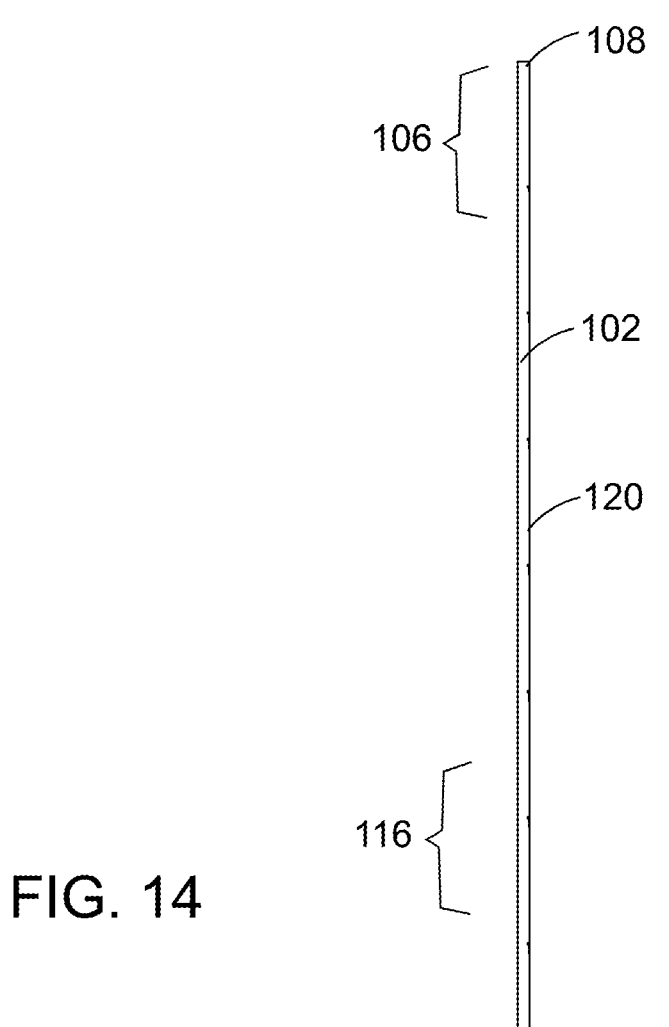
FIG. 14 is a rear view of the inner tube, according to at least one embodiment of the present disclosure.

As can be seen in FIGS. 13 and 14, the assembly 100 may
comprise an inner tube 102 configured as an ETE body,
which may include a proximal portion 106 defining a
proximal opening 108, and a distal portion 110 defining a
distal opening 112. The inner tube 102 may also define a
bottom oxygen passage hole at a distal end of the distal
portion 110 to deliver gas even if the main opening may be
occluded. The inner tube 102 may be positioned to be
slidably receivable within the primary lumen of the ETT
104. The inner tube 102 may extend along a longitudinal
axis and/or has an overall length greater than the ETT 104,
for example, on the order of slightly more than twice the
length of the ETT 104, such that the inner tube may protrude
proximally from the ETT 104 when its distal portion 110
may be aligned near the distal tip of the ETT 104. The inner
tube 102 may define an internal flow passage extending
continuously from a proximal portion 106 to a distal portion
110, and/or has a bottom oxygen passage hole at the distal
end. The outer diameter of the inner tube 102 may be less
than the inner diameter of the ETT 104, such that an annular
clearance between the inner tube outer surface and the ETT
inner surface when the inner tube may be slidably received
within the ETT lumen. At a proximal portion 106 of the
inner tube 102, a top connector 122 may be secured to the
inner tube 102. This top connector 122 may comprise a
generally tubular body having a distal attachment portion
that may be fitted to the proximal opening 108 of the inner
tube 102. The top connector may be sized to mate with a
standard ventilator connector (VC) and/or a standard ETT
104.

Figure 2:
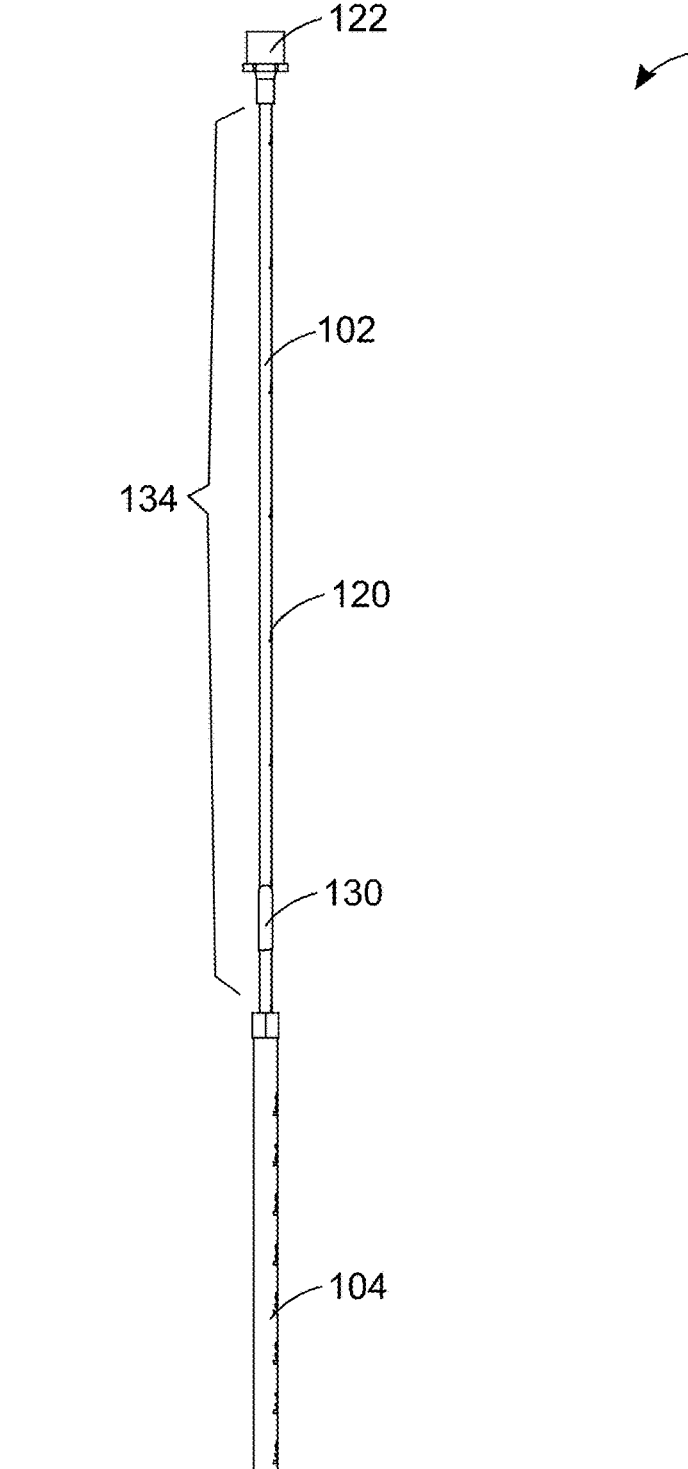
FIG. 2 is a front view of the inner tube advanced toward the distal tip of the ETT while the top connector is removably coupled to the proximal opening of the inner tube, showing how the ETT can slide along the inner tube, according to at least one embodiment of the present disclosure.
Figure 3:
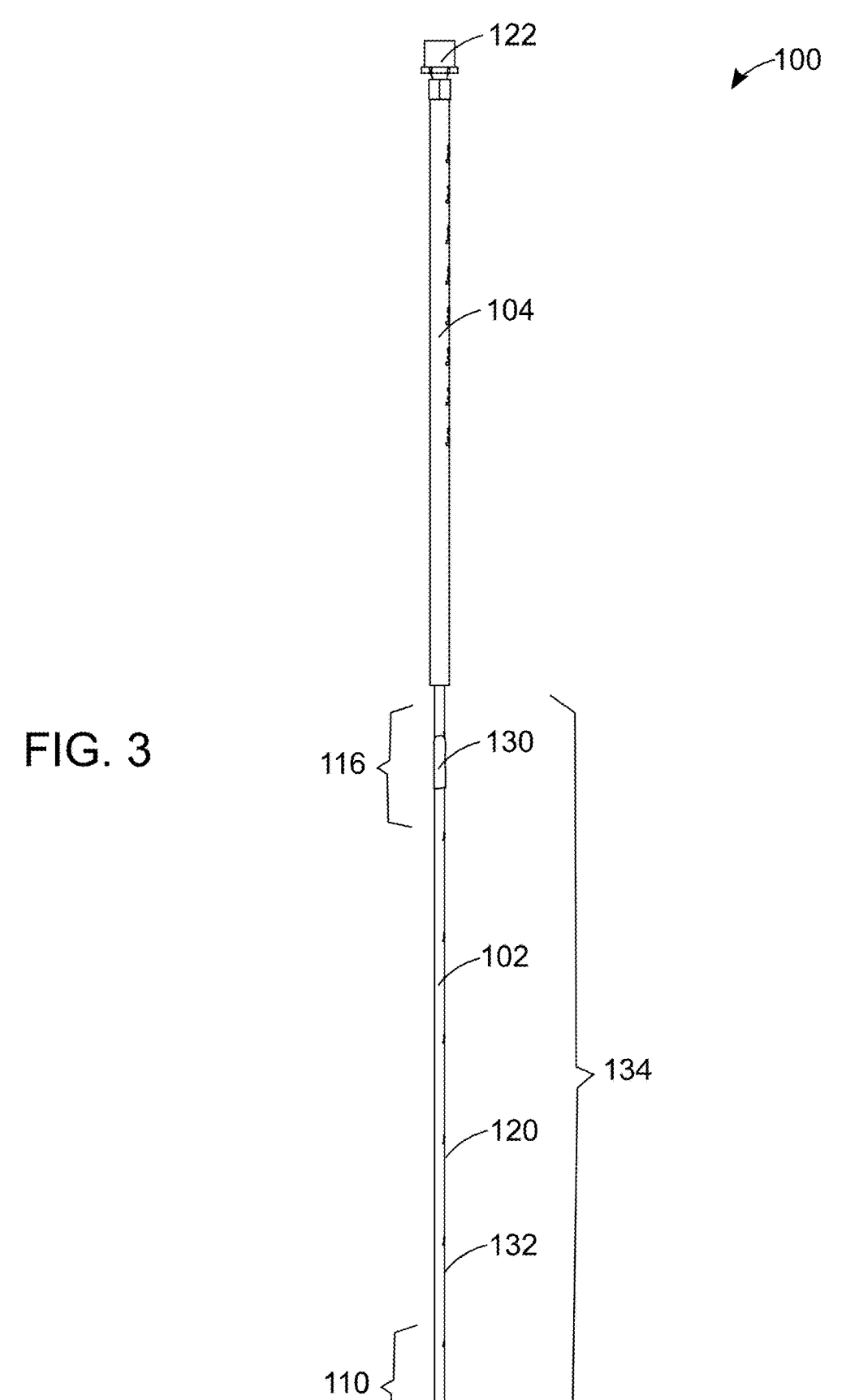
FIG. 3 is a front view of the outer ETT slid proximally along the inner tube until the proximal end of the ETT is adjacent to the top connector of the ETE, according to at least one embodiment of the present disclosure.

As can be seen in FIGS. 1, 3, and 13, the inner tube 102
may include an intermediate region 116 spaced from the
proximal portion 106 and the distal portion 110. At an
intermediate region 116 of the inner tube 102, spaced from
the proximal end and the distal end of the inner tube 102, the
wall 120 of the inner tube 102may define a lateral side
opening 118. As shown in FIG. 13, this opening 118 may be
bounded by a continuous edge of the inner tube wall 120. As
shown in FIGS. 1-3, a cover 130 such as an elongate tape
may be dimensioned and/or arranged to conform to the outer surface contour of the inner tube 102 around this interme-
diate region 116. The tape, preferably an elongate rectan-
gular or oval shape though its design may take other shapes
such as a circular or polygonal shape, may be configured to
be wrapped and/or adhered circumferentially around the
outer surface of the inner tube 102 so that it may overlie the
bounded area of the lateral side opening 118 and/or contacts
the surrounding wall region on all sides, to form a continu-
ous outer wall surface 134 at the region. Thus, the cover 130
may help prevent air from escaping through the lateral side
opening 118.

Figure 4:
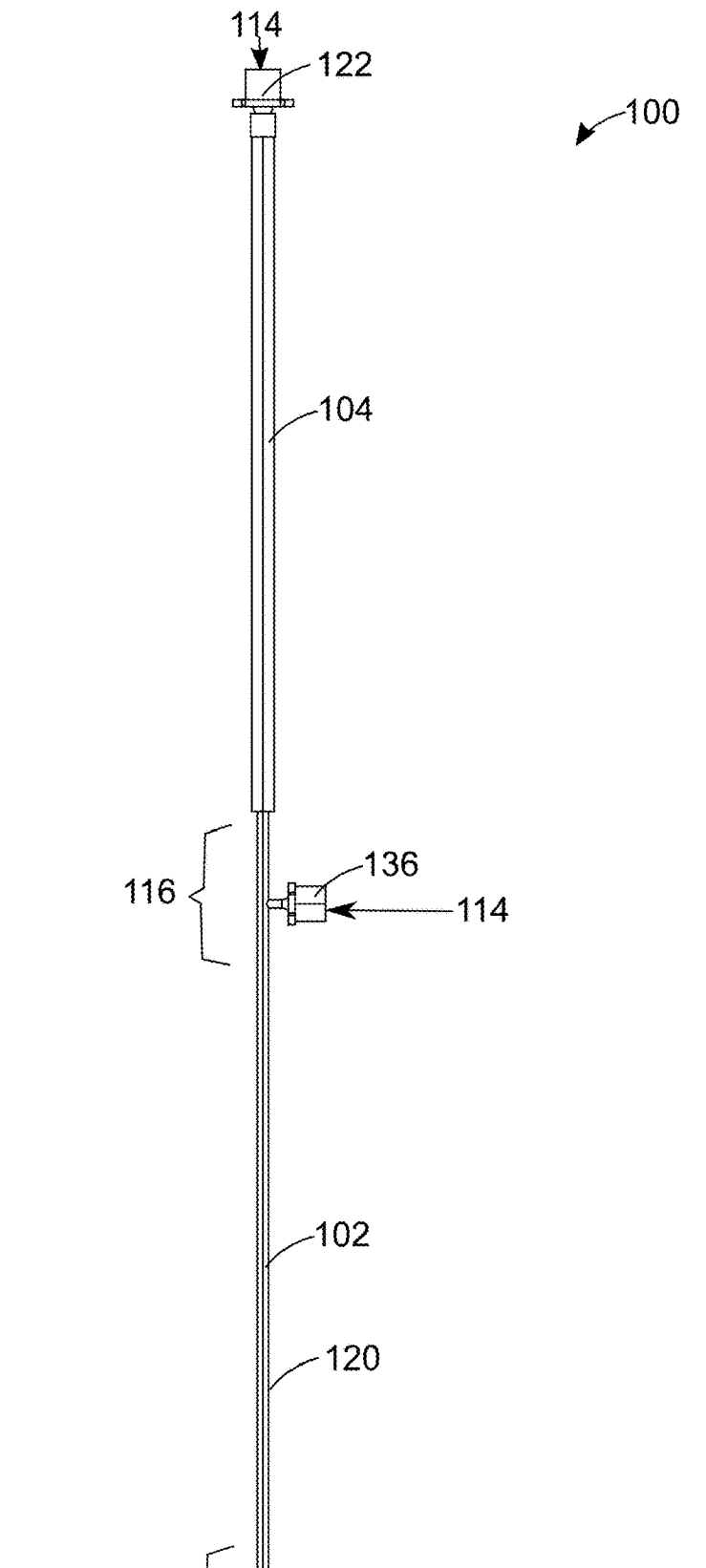
FIG. 4 is a left side view of the ETE assembly after the cover has been removed from the lateral side opening and a side adapter has been inserted into the lateral side opening, according to at least one embodiment of the present disclosure.
Figure 5:
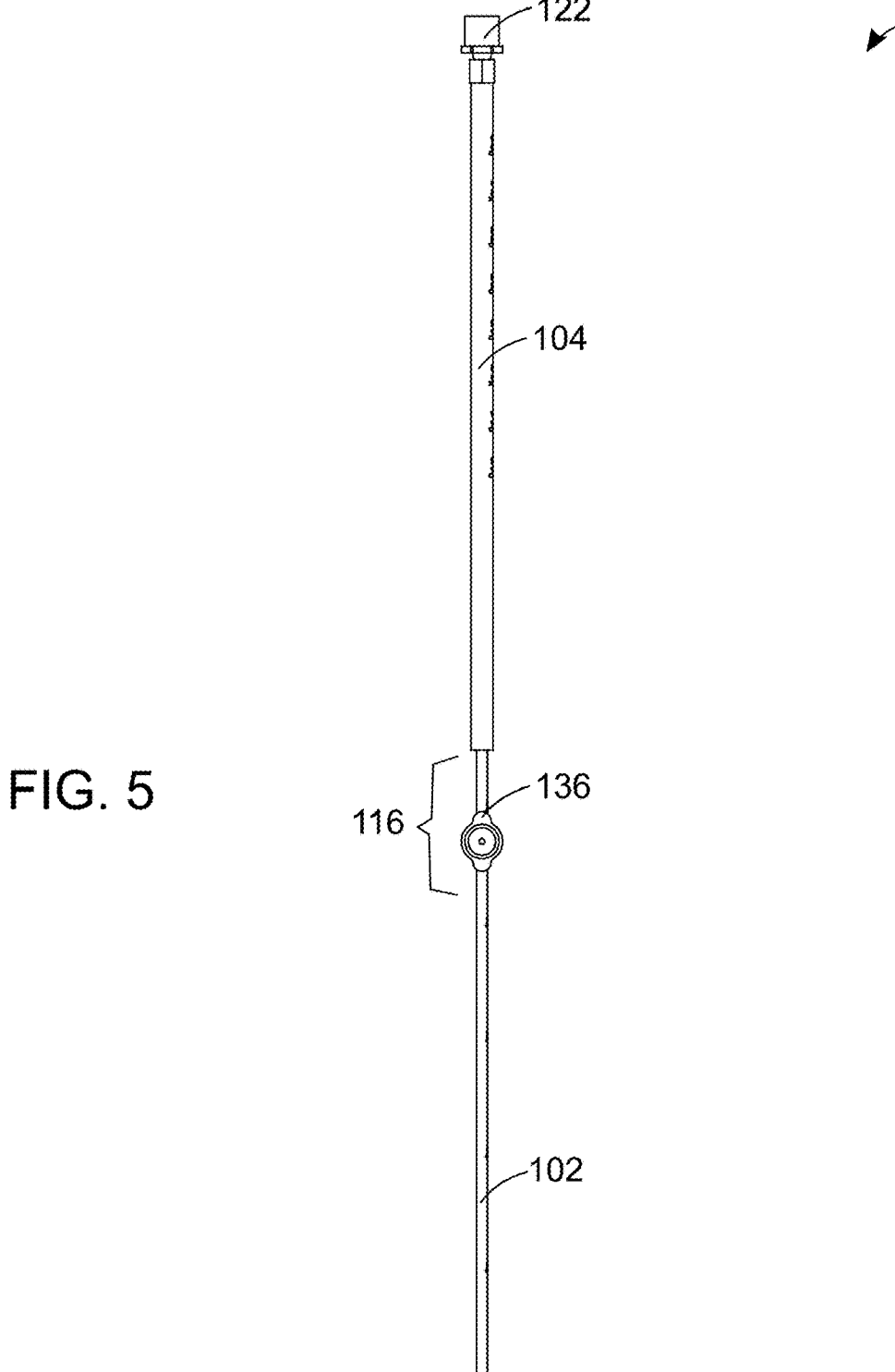
FIG. 5 is a front view of the ETE assembly after the cover has been removed from the lateral side opening and a side adapter has been inserted into the lateral side opening, according to at least one embodiment of the present disclosure.
Figure 6:
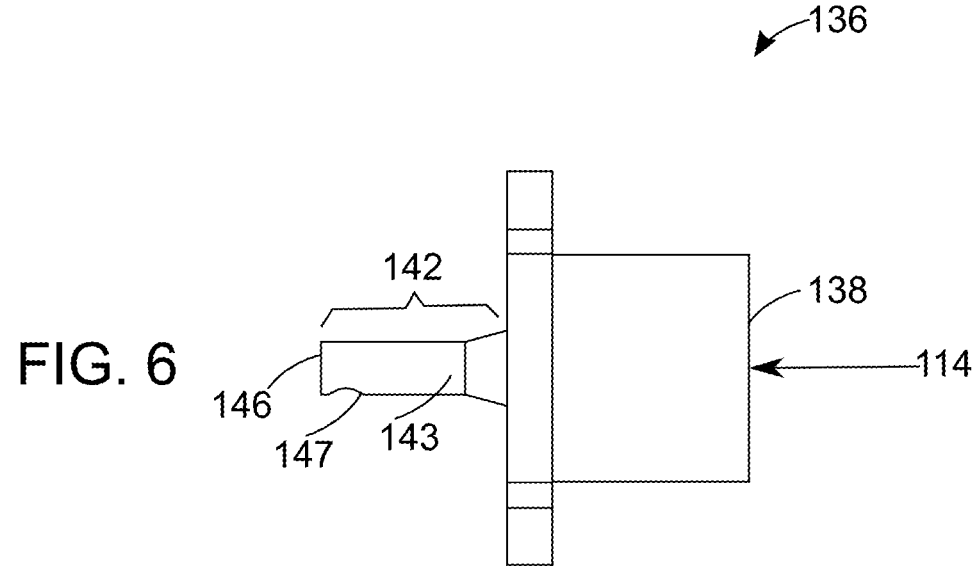
FIG. 6 is a left side view of the side adapter, according to at least one embodiment of the present disclosure.
Figure 7:
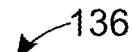
FIG. 7 is a top plan view of the side adapter, according to at least one embodiment of the present disclosure.
Figure 7:
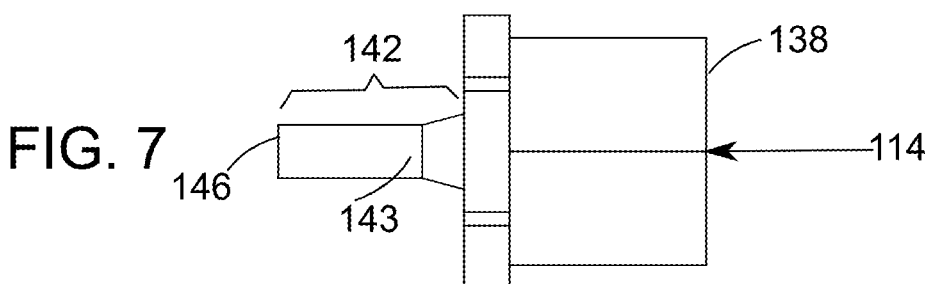
Figure 8:
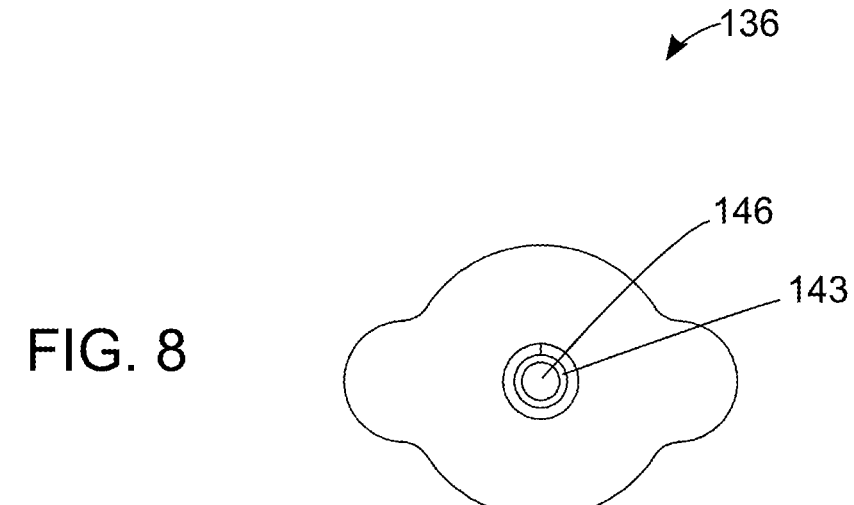
FIG. 8 is a rear view of the side adapter, according to at least one embodiment of the present disclosure.
Figure 9:
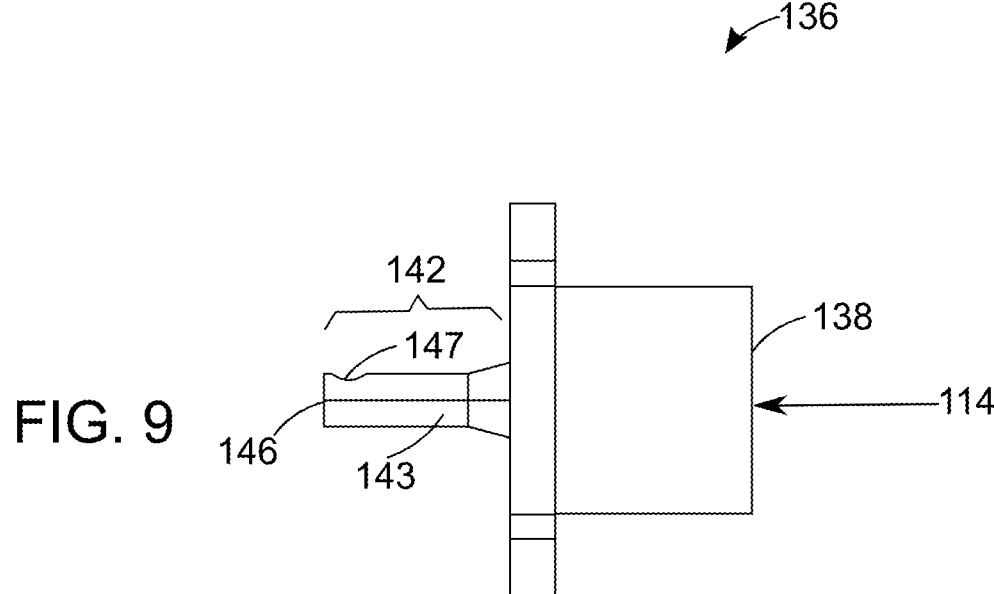
FIG. 9 is a left side view of the side adapter, shown rotated 180 degrees relative to the orientation in FIG. 6, according to at least one embodiment of the present disclosure.
Figure 10:
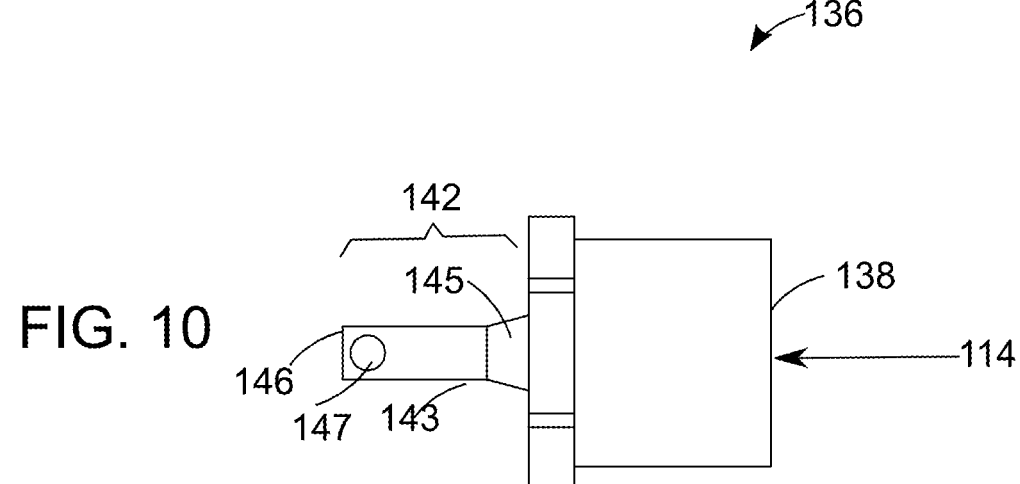
FIG. 10 is a bottom plan view of the side adapter, according to at least one embodiment of the present disclosure.
Figure 11:
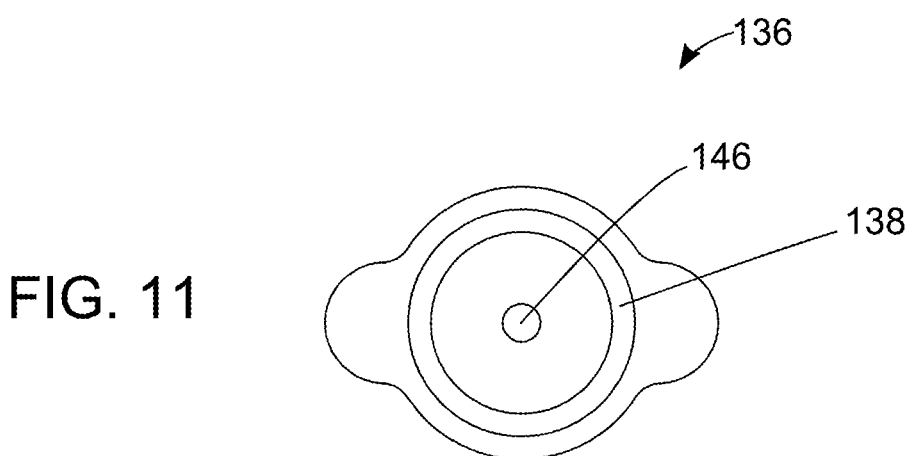
FIG. 11 is a front view of the side adapter, according to at least one embodiment of the present disclosure.
Figure 12:
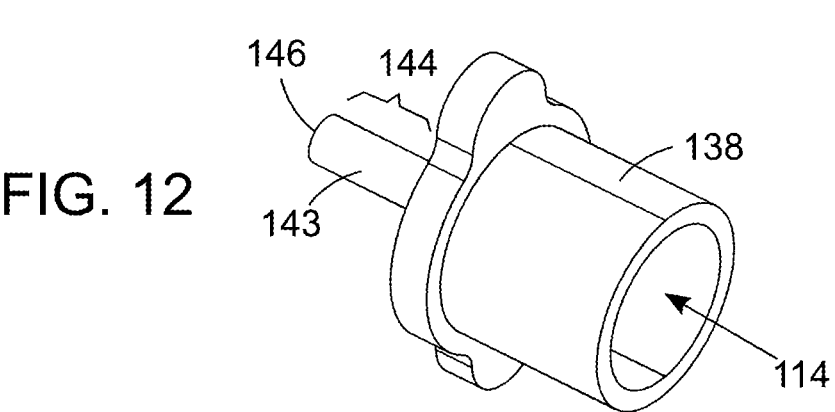
FIG. 12 is a front-top perspective view of the side adapter, according to at least one embodiment of the present disclosure.

Referring to FIGS. 4-5, a side adapter 136 may be
configured to be attachable to the inner tube 102 at the
intermediate region 116 where the lateral side opening 118
may reside once the cover 130 may be removed. That is, the
cover 130 and the side adapter 136 may be alternatively
positioned around the same bounded lateral side opening
118 region. As can be seen in FIGS. 6-12, the side adapter
136 may comprise an outer connector portion 138 having a
shape substantially similar to the proximal top connector
122, dimensioned to accept a VC. The side adapter 136 may
further include an elongate insertion portion 142 extending
inwardly from the connector portion. This insertion portion
142 may be sized to be received through the lateral side
opening 118 of the inner tube 102 and/or into the internal
passage of the inner tube. In a preferred embodiment, the
insertion portion 142 and/or the lateral side opening 118,
when viewed in cross section, may be circular because this
shape may minimize sharp edges and/or facilitate smooth
insertion of the side adapter 136 through the lateral side
opening 118 and/or into the inner tube's internal passage.
However, in other embodiments, the insertion portion 142
and/or the lateral side opening 118 may be of any other
suitable shape that may allow for proper sealing and/or fluid
flow, such as oval, elliptical, or polygonal.

As illustrated in FIGS. 6-10 and 12, the insertion portion
142 may be bounded by a surrounding wall 143 that may
define an internal channel continuous with the outer con-
nector portion 138. This internal channel may terminate at
the inner end 145 of the insertion portion 142, where the
surrounding wall 143 may define two distinct openings.
First, the wall 143 of the insertion portion 142 may form a
distal outlet opening 146 at the terminal tip of the insertion
portion 142, oriented along the axis of insertion to be
received through the lateral side opening 118 of the inner
tube 102. Second, the wall 143 may define an aperture 147
located on an axis perpendicular to the distal outlet opening
146. Specifically, the aperture 147 may be located on the
bottom surface of the insertion portion 142. In this configu-
ration, the aperture 147 may face the direction of the airway,
so that gas flow may be directed primarily toward the distal
opening 112 of the inner tube 102. The side adapter 136 may
be positioned within the internal passage of the inner tube
102 such that gas entering the outer connector portion 138
may flow through the internal channel. The inner tube 102
may be dimensioned such that, when its distal opening 112
approaches the distal end of the ETT 104, the proximal
opening of the ETT 104 and the intermediate lateral side
opening 118 may be located outside the patient's airway.
The lateral side opening 118 may be located at a fixed
distance from the proximal end of the inner tube, so that, in
use, the side adapter 136 can be coupled at an intermediate
position relative to the proximal opening.

In accordance with another aspect of the disclosure, the
assembly 100 according to the present disclosure may be
provided as an endotracheal tube exchanger kit, comprising
components shown in FIGS. 1-14. The kit may comprise the components necessary for the exchange procedure 1500, packaged together for convenient clinical use. As described above, the kit may include the inner tube 102, the top connector 122 which may be secured thereto, the removable cover 130 (such as the tape element), and/or the side adapter 136. The side adapter 136 may be provided separate from the inner tube 102 within the kit. In certain embodiments, the components, including the inner tube 102, top connector 122, removable cover 130, and/or side adapter 136, may be sterilized and/or enclosed within a sealed sterile package to maintain sterility until use. Furthermore, specific components may have their own protection; for example, the side adapter 136 may be sealed within a packaging enclosure separate from the inner tube 102 but contained within the main kit, or the removable cover 130 such as a tape element may be provided with its peelable backing layer intact to preserve the adhesive surface. The tape element may be designed for ease of removal and/or provide an adhesive surface and/or a peelable backing layer covering the adhesive surface. The backing layer may be removable to expose the adhesive surface for application to the inner tube 102, acting similarly to a bandage to seal the lateral side opening 118 until access may be required. This kit configuration may allow that all necessary parts, such as the side adapter 136 with its elongate insertion portion 142 and/or outer connector portion 138, may be readily available to the clinician during the time-sensitive exchange procedure.

Figure 15B:
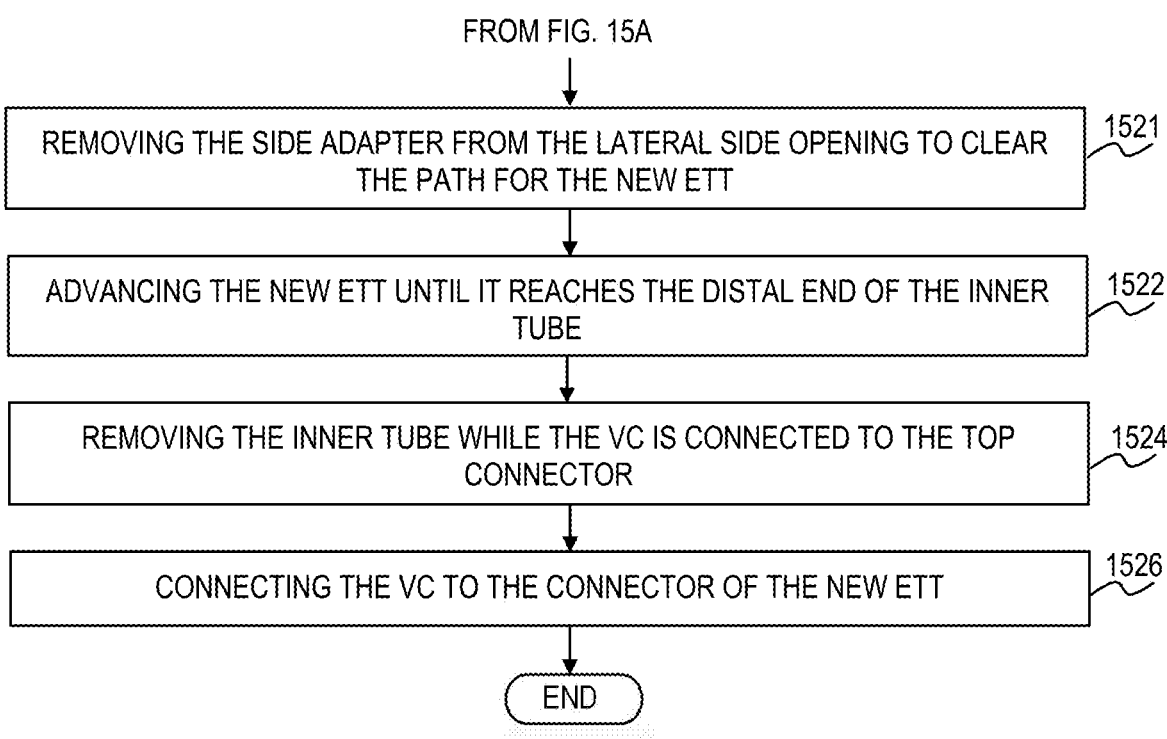

In FIGS. 15A and 15B, a sequence of steps for exchanging an ETT 104 is illustrated, according to at least one embodiment of the present disclosure. The ETE assembly 100 of the present disclosure may be used in a method for ETT exchange, so that it may provide a safer exchange of the ETT 104 by maintaining oxygen flow from the ventilator to the patient during the procedure. At step 1502, the process may commence by disconnecting the ventilator (VC) from the old ETT 104 and at step 1504 immediately connecting the VC to the top connector 122. Air then may flow through the ETE through the top connector 122. At step 1506, the inner tube (ETE) 102 may be introduced inside the old ETT 104 and advanced until it may reach a certain depth, generally at the level of the ETT lower tip, with the patient continuing to receive air via the top connector 122. At step 1508, the old ETT may be then slid up until it may reach the top connector 122. Then, at step 1510 the cover may be removed, and at step 1512 the side adapter 136 connected to the lateral side opening 118 of the inner tube 102. Subsequently, at step 1514, the VC may be disconnected from the top connector 122 and connected to the side adapter 136. At step 1516, the old ETT 104 may be removed via the proximal end. At step 1518, a new ETT 104 may be then loaded onto the ETE 102 via the proximal end and slid in until it reaches the level of the intermediate region 116 of the inner tube 102. At step 1520, once the new ETT 104 reaches the intermediate region 116, the VC may be disconnected from the side port and reconnected to the top connector 122. At step 1521, the side adapter 136 may be then removed from the lateral side opening 118 to clear the path for the new ETT 104. At step 1522, the new ETT 104 may be advanced until it reaches the distal portion 110 of the inner tube 102. Once the new ETT 104 position is secured, the ETE 102 may be removed while the VC remains connected to the top connector at step 1524. When the ETE 102 is completely withdrawn, at step 1526 the VC may be connected to the connector of the new ETT 104. While the steps in FIGS. 15A and 15B are shown in a particular exemplary order, it is appreciated that the individual steps may be reordered, omitted, and/or repeated.

Compared with the prior art, the present disclosure may offer a substantial improvement in patient safety and/or procedural efficacy during endotracheal tube (ETT) exchange by providing oxygenation and/or ventilation with minimal interruption throughout the entire process. Unlike conventional methods that may necessitate disconnecting the patient from the ventilator for a longer period of time, which may create dangerous intervals without adequate gas delivery, the disclosed assembly may utilize an inner tube 102 with a proximal opening 108 and an intermediate lateral side opening 118 to facilitate the use of a top connector 122 and a side adapter 136. This arrangement may allow the ventilator connector to be interchangeably coupled to the proximal opening 108 and/or the side adapter 136, so that airflow can be maintained and/or health risks can be minimized. Furthermore, the disclosed system may provide a cost-effective and/or easy-to-use assembly, helping to reduce procedural complexity and/or improve outcomes for patients with reduced respiratory capacity.

Although the invention has been explained in relation to its preferred embodiment, it is to be understood that many other possible modifications and variations can be made without departing from the spirit and scope of the invention. Other technical advantages may become readily apparent to one of ordinary skill in the art after review of the figures and description. It should be understood that, although exemplary embodiments are illustrated in the figures and described above, the principles of the present disclosure may be implemented using any number of techniques, whether currently known or not. The present disclosure should in no way be limited to the exemplary implementation and techniques illustrated in the drawings and description above.

Well-known methods, procedures, and/or components have not been described in detail so as not to obscure the principles of the example embodiments. Except as stated immediately above, nothing that has been stated or illustrated is intended or should be interpreted to dedicate any component, step, feature, object, benefit, advantage, or equivalent to the public, regardless of whether it is or is not recited in the claims issuing herefrom. Unless explicitly stated, the example systems, methods, and/or processes described herein are neither constrained to a particular order or sequence nor constrained to a particular system configuration. Additionally, some of the described embodiments or elements thereof can occur or be performed simultaneously, at the same point in time, and/or concurrently. Thus, for example, any sequence(s) and/or temporal order of steps of various processes or methods that are described herein are illustrative and not restrictive. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

The present disclosure includes many aspects and features. Certain features that are described in this specification in the context of separate embodiments can also be implemented in combination or in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Any embodiment discussed and identified as being "preferred" or "exemplary" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure. While the foregoing has described what are considered to be the best mode or other examples, it is understood that various modifications may be made, the subject matter disclosed may be implemented in various forms and examples, and the teachings may be applied in numerous applications, only some of which have been described.

The scope of protection is intended and should be interpreted to be as broad as is consistent with the ordinary meaning of the language when interpreted in light of this specification and the prosecution history and to encompass all structural and functional equivalents. It will be understood that the terms and expressions used have the ordinary meaning as is accorded to such terms and expressions with respect to their corresponding respective areas of inquiry and study, except where specific meanings have been otherwise set forth. To the extent that the meaning of a term used herein, as understood by the ordinary artisan based on the contextual use of such term, differs in any way from any particular dictionary definition of such term, it is intended that the meaning of the term as understood by the ordinary artisan should prevail. The terms and words as used herein, including technical or scientific terms, may have the same meanings as generally understood by those skilled in the art. The terms as generally defined in dictionaries may be interpreted as having the same or similar meanings as or to contextual meanings of the relevant art. Unless otherwise defined, the terms should not be interpreted as ideally or excessively formal meanings. Even though a term is defined in the disclosure, the term should not be interpreted as excluding embodiments of the disclosure under circumstances.

Unless otherwise stated, all measurements, values, ratings, positions, magnitudes, sizes, and other specifications that are set forth in this specification are approximate, not exact. They are intended to have a reasonable range that is consistent with the functions to which they relate and with what is customary in the relevant field. In interpreting a numerical value, the value is interpreted as including an error range unless there is no separate explicit description thereof. In addition, disclosure of ranges includes disclosure of all values and further divided ranges within the entire range, including endpoints and sub-ranges given for the ranges. All numerical values of parameters (e.g., of quantities or conditions) in this specification are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%. A shape, a size, a ratio, an angle, a number, etc. disclosed in the drawings for illustrating embodiments of the present disclosure are exemplary, and the present disclosure is not limited thereto. The size and thickness of each configuration shown in the drawings are arbitrarily shown for better understanding and ease of description, but the present invention is not limited thereto. In the drawings, the thickness of layers, films, panels, regions, etc., are exaggerated for clarity. For ease of description, the thicknesses of some layers and areas are exaggerated.

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, as used herein, the expression "A and/or B" means "A, B or both of them". As used herein, each of such phrases as "A or B", "at least one of A and B", "at least one of A or B", "A, B, or C", "at least one of A, B, and C", and "at least one of A, B, or C" may include any one of, or all possible combinations of the items enumerated together in a corresponding one of the phrases (e.g., A alone, B alone, C alone, A and B together, A and C together, B and C together, and/or A, B, and C together, etc.). Furthermore, relational terms such as "first" and "second" and the like may be used solely to distinguish one entity or action from another without necessarily requiring or implying any actual relationship or order between such entities or actions. It is to be understood that if an element (e.g., a first element) is referred to, with or without the term "operatively" or "communicatively", as "coupled with", "coupled to", "connected with", or "connected to" another element (e.g., a second element), it means that the element may be coupled with the other element directly (e.g., wiredly), wirelessly, or via a third element. In descriptions of temporal relationships, for example, temporal precedent relationships between two events such as "after", "subsequent to", "before", etc., another event can occur therebetween unless "directly after", "directly subsequent" or "directly before" is indicated. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, the drawings are intended to be read together with the specification and are to be considered a portion of the entire written description of this present disclosure. Spatially relative terms, such as "beneath," "below," "lower," "under," "above," "upper," and the like, can be used herein for ease of explanation to describe one element or feature's relationship to another element or feature as illustrated in the figures. It will be understood that the spatially relative terms are intended to encompass different orientations of the apparatus in use or in operation, in addition to the orientation depicted in the figures. For example, when the apparatus in the drawings can be turned over, elements described as "below" or "beneath" or "under" other elements or features would then be oriented "above"

the other elements or features. Thus, the example terms "below" and "under" can encompass both an orientation of above and below. The apparatus can be otherwise oriented for example, rotated 90 degrees or at other orientations, and the spatially relative descriptors used herein should be interpreted accordingly. As used in the following description, the terms "horizontal", "vertical", "left", "right", "up", "down", and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly", "outwardly", and "radially" generally refer to the orientation of a surface relative to its axis of elongation, or axis of rotation, as appropriate. As used herein, the term "dorsal" refers to positions that are located near, on, or towards the upper or top surface of a structure. In addition, it will also be understood that when an element or layer is referred to as being "between" two elements or layers, it can be the only element or layer between the two elements or layers, or one or more intervening elements or layers can also be present. In addition, it will also be understood that when a first element or layer is referred to as being present "on" or "beneath" a second element or layer, the first element can be disposed directly on or beneath the second element or can be disposed indirectly on or beneath the second element with a third element or layer being disposed between the first and second elements or layers.

What is claimed is:

1. An endotracheal tube exchanger assembly comprising:
an inner tube extending along a longitudinal axis, including:
a proximal portion defining a proximal opening;
a distal portion defining a distal opening;
an internal flow passage extending continuously from the proximal opening to the distal opening; and
an intermediate region spaced from the proximal portion and the distal portion, the intermediate region defining a lateral side opening bounded by a wall of the inner tube;
a top connector secured to the proximal portion of the inner tube, the top connector including a tubular body aligned with the internal flow passage;
a removable cover disposed about the intermediate region of the inner tube, the removable cover conforming to an outer surface of the inner tube to seal the lateral side opening; and
a side adapter separate from the inner tube and configured to be received within the lateral side opening, the side adapter including:
an outer connector portion dimensioned to couple with a ventilator connector; and
an elongate insertion portion extending inwardly from the outer connector portion, the elongate insertion portion defining an internal channel in fluid communication with the outer connector portion.

2. The endotracheal tube exchanger assembly of claim 1, wherein the elongate insertion portion defines an aperture that faces toward a distal direction of the inner tube.

3. The endotracheal tube exchanger assembly of claim 2, wherein the elongate insertion portion further defines a distal outlet opening.

4. The endotracheal tube exchanger assembly of claim 3, wherein the internal channel of the side adapter is configured to direct gas flow primarily toward the distal opening of the inner tube.

5. The endotracheal tube exchanger assembly of claim 3, further including an endotracheal tube, wherein the inner tube has an overall length that is greater than twice a length of the endotracheal tube.

6. The endotracheal tube exchanger assembly of claim 5, wherein an outer diameter of the inner tube is less than an inner diameter of the outer endotracheal tube to define an annular clearance.

7. The endotracheal tube exchanger assembly of claim 1, wherein the lateral side opening has a circular cross-sectional shape.

8. The endotracheal tube exchanger assembly of claim 7, wherein the removable cover comprises an elongate tape element.

9. The endotracheal tube exchanger assembly of claim 8, wherein the elongate insertion portion of the side adapter extends into the internal flow passage of the inner tube.

10. The endotracheal tube exchanger assembly of claim 9, wherein the top connector includes a distal attachment portion fitted to the proximal portion of the inner tube.

11. The endotracheal tube exchanger assembly of claim 10, wherein the top connector defines an internal bore that aligns with the internal flow passage of the inner tube.

12. The endotracheal tube exchanger assembly of claim 10, wherein the lateral side opening is bounded by a continuous edge of the inner tube wall.

13. The endotracheal tube exchanger assembly of claim 9, wherein the removable cover conforms to an outer surface contour of the inner tube to form a continuous outer wall surface.

14. A method of exchanging an endotracheal tube, comprising the steps of:
providing an endotracheal tube exchanger assembly comprising:
an inner tube including a proximal portion defining a proximal opening, a distal portion defining a distal opening, an internal flow passage extending continuously from the proximal opening to the distal opening, and an intermediate region defining a lateral side opening;
a top connector secured to the proximal portion of the inner tube;
a removable cover sealing the lateral side opening; and
a side adapter separate from the inner tube and configured to be received within the lateral side opening;
disconnecting a ventilator from an existing endotracheal tube;
connecting the ventilator to the top connector of the provided endotracheal tube exchanger assembly;
introducing the inner tube inside the existing endotracheal tube and advancing the inner tube inside the existing endotracheal tube;
sliding the existing endotracheal tube proximally along the inner tube until the existing endotracheal tube reaches the top connector;
removing the removable cover from the lateral side opening of the inner tube;
connecting the side adapter to the lateral side opening;
disconnecting the ventilator from the top connector and connecting the ventilator to the side adapter;
removing the existing endotracheal tube via a proximal end of the inner tube;
loading a new endotracheal tube onto the inner tube via the proximal end and sliding the new endotracheal tube until the new endotracheal tube reaches the intermediate region of the inner tube;

disconnecting the ventilator from the side adapter and reconnecting the ventilator to the top connector;

removing the side adapter from the lateral side opening;

advancing the new endotracheal tube until the new endotracheal tube reaches the distal portion of the inner tube;

removing the inner tube from the new endotracheal tube; and connecting the ventilator to the new endotracheal tube.

15. An endotracheal tube exchanger kit comprising:

an inner tube extending along a longitudinal axis; including:

a proximal portion defining a proximal opening;

a distal portion defining a distal opening;

an internal flow passage extending continuously from the proximal opening to the distal opening; and an intermediate region spaced from the proximal portion and the distal portion, the intermediate region defining a lateral side opening bounded by a wall of the inner tube;

a top connector secured to the proximal portion of the inner tube, the top connector including a tubular body aligned with the internal flow passage;

a removable cover comprising a tape element disposed about the intermediate region of the inner tube, wherein the tape element forms a continuous outer wall surface at the intermediate region to seal the lateral side opening; and a side adapter separate from the inner tube and configured to be received within the lateral side opening, the side adapter including:

an outer connector portion dimensioned to couple with a ventilator connector; and an elongate insertion portion extending inwardly from the outer connector portion, the elongate insertion portion defining an internal channel in fluid communication with the outer connector portion, wherein the elongate insertion portion defines an aperture that faces toward the distal direction of the inner tube.

16. The endotracheal tube exchanger kit of claim 15, wherein the side adapter is configured to be slidably received within the lateral side opening.

17. The endotracheal tube exchanger kit of claim 16, wherein the elongate insertion portion further defines a distal outlet opening at a terminal tip thereof, and wherein the aperture is located on a bottom surface of the elongate insertion portion on an axis perpendicular to the distal outlet opening.

18. The endotracheal tube exchanger kit of claim 17, further including an endotracheal tube.

19. The endotracheal tube exchanger kit of claim 18, further comprising a packaging enclosure, wherein the inner tube, the endotracheal tube, the side adapter, and the removeable cover are sealed within the packaging enclosure.

20. The endotracheal tube exchanger kit of claim 15, wherein the inner tube, the endotracheal tube, the top connector, the removable cover, and the side adapter are sterilized and enclosed within a sealed sterile package.

\* \* \* \* \*